United States Patent [19]

Currans

[11] 4,351,181

[45] Sep. 28, 1982

[54] LINEAR, GAS TO VOLTAGE TRANSDUCER CIRCUIT

[76] Inventor: James H. Currans, 4089 W. Chenango Ave., Littleton, Colo. 80123

[21] Appl. No.: 198,117

[22] Filed: Oct. 17, 1980

[51] Int. Cl.³ .......................................... G01N 27/12
[52] U.S. Cl. ........................................ 73/23; 340/634
[58] Field of Search ................. 73/23, 27 R; 340/634; 324/71 SN; 422/98

[56] References Cited

U.S. PATENT DOCUMENTS

| | | | |
|---|---|---|---|
| 3,887,908 | 6/1975 | Swigert | 340/634 |
| 3,997,837 | 12/1976 | Betz et al. | 73/27 R |
| 4,019,367 | 4/1977 | Norsworthy | 73/23 |
| 4,112,356 | 9/1978 | Toy | 73/27 R |
| 4,185,491 | 1/1980 | Owen | 73/27 R |

FOREIGN PATENT DOCUMENTS 2629576  1/1978  Fed. Rep. of Germany .......... 73/23

Primary Examiner—Stephen A. Kreitman
Attorney, Agent, or Firm—Jack C. Sloan

[57] ABSTRACT

In a gas sensor circuit having a semiconductor gas measuring sensor such as a Taguchi, a variable gain transconductance amplifier is interconnected between the gas measuring sensor and a conventional differential amplifier so that the circuit's output voltage appears as a linear function of the gas concentration being measured.

10 Claims, 3 Drawing Figures

LINEAR, GAS TO VOLTAGE TRANSDUCER CIRCUIT

BACKGROUND OF THE INVENTION

The present invention relates to gas sensor circuits employing semiconductors as the sensor element. It is known that the electrical resistance of certain semiconductor materials, such as tin dioxide for example, vary in accordance with the concentration of certain gas atmospheres, e.g., carbon monoxide, hydrogen, methane, etc. into which said semiconductors are placed and that it is therefore possible to utilize this transducer property of the semiconductor in gas sensor circuits. Examples of such prior art gas sensor circuits are found in U.S. Pat. Nos. 4,112,356 and 3,997,837. These circuits are characterized by the fact that the voltage output of the sensor is directly connected to the positive input terminal of a conventional differential amplifier (CDA). Unfortunately, a sensor's output voltage is often non-linear over a wide range of gas concentrations and hence the output signal of the CDA is also non-linear. Furthermore, this non-linear output often varies according to curves which are not easily defined mathematically.

This non-linearity has heretofore presented the prior art with a number of problems, expenses and work inconveniences. For example, since the output of the prior art circuit is non-linear, any output measuring device such as a voltmeter must be specially made or specially calibrated in order to accurately relate a gas concentration to a given voltage. On the other hand, if a linear output were being produced by such a gas sensor circuit then standard voltmeters could be used to measure the linear gas concentration to voltage relationship without need for the expensive calibration techniques required to measure a non-linear relationship.

Problems associated with the use of non-linear output signals are particularly evident in systems applications where such signals are to be fed to a computer. Because both analog and digital computers can directly use a linear input without the need for storing the calibration information associated with a non-linear relationship, great inconvenience and expenses can be avoided if the computer can be fed a linear signal. Therefore, rather than trying to follow such curves electronically most prior art gas sensor circuits were designed to operate above a certain discrete voltage point and to cease to operate below that same voltage point. Such single point activations severely limit the system's versatility because these single point circuits will not operate at gas concentrations lower than that necessary to lower the semiconductor's output voltage to the circuit's activation point. On the other hand, setting the voltage activation point to higher values may result in unnecessary operation of equipment such as parking garage exhaust fans, which are subsequently connected to the gas sensor circuit's voltage output. Heretofore, the solution to this dilemma has been to either be satisfied with one arbitrary operation point or to construct the sensor circuit with a series of different discrete voltage activation points or, in the systems situation, to store the non-linear curve information in the computer. Naturally, such solutions to the problem are more complex, and hence more costly.

U.S. Pat. No. 4,185,491 deals with the problem of non-linear output of such gas sensor units by connecting a known bridge type linearization circuit to its comparator amplifier and to its two differential amplifiers in order to achieve its purpose of avoiding unnecessary operation of the sensor at reduced temperatures in order to prevent sensor poisoning which occurs by the more rapid absorption of gas at lower temperatures. Known bridge linearization circuits of the type employed in this patent for the purpose of reducing operation of the sensor at reduced temperatures are also relatively complex and costly.

SUMMARY OF THE PRESENT INVENTION

It is therefore a principal object of the present invention to provide an improved semiconductor gas sensor circuit having a simplified method for obtaining a linear gas concentration to voltage relationship which subsequently can be easily detected, measured and used by other external operation performing components of the circuit such as exhaust fans, valves, alarms, meters, recorders, computers, etc. This linearization of the output of a gas sensor circuit is particularly useful where the external operation performing components such as exhaust fans are to be used individually, or in unison depending on the gas concentrations to be removed. These and other objects of this invention are achieved by a circuit whose main feature is the connection of the output voltage signal of the gas sensor to a variable gain transconductance amplifier (VGTA) before the output voltage signal is subsequently fed to a conventional differential amplifier (CDA).

DESCRIPTION OF THE PREFERRED EMBODIMENTS

Figure 1:
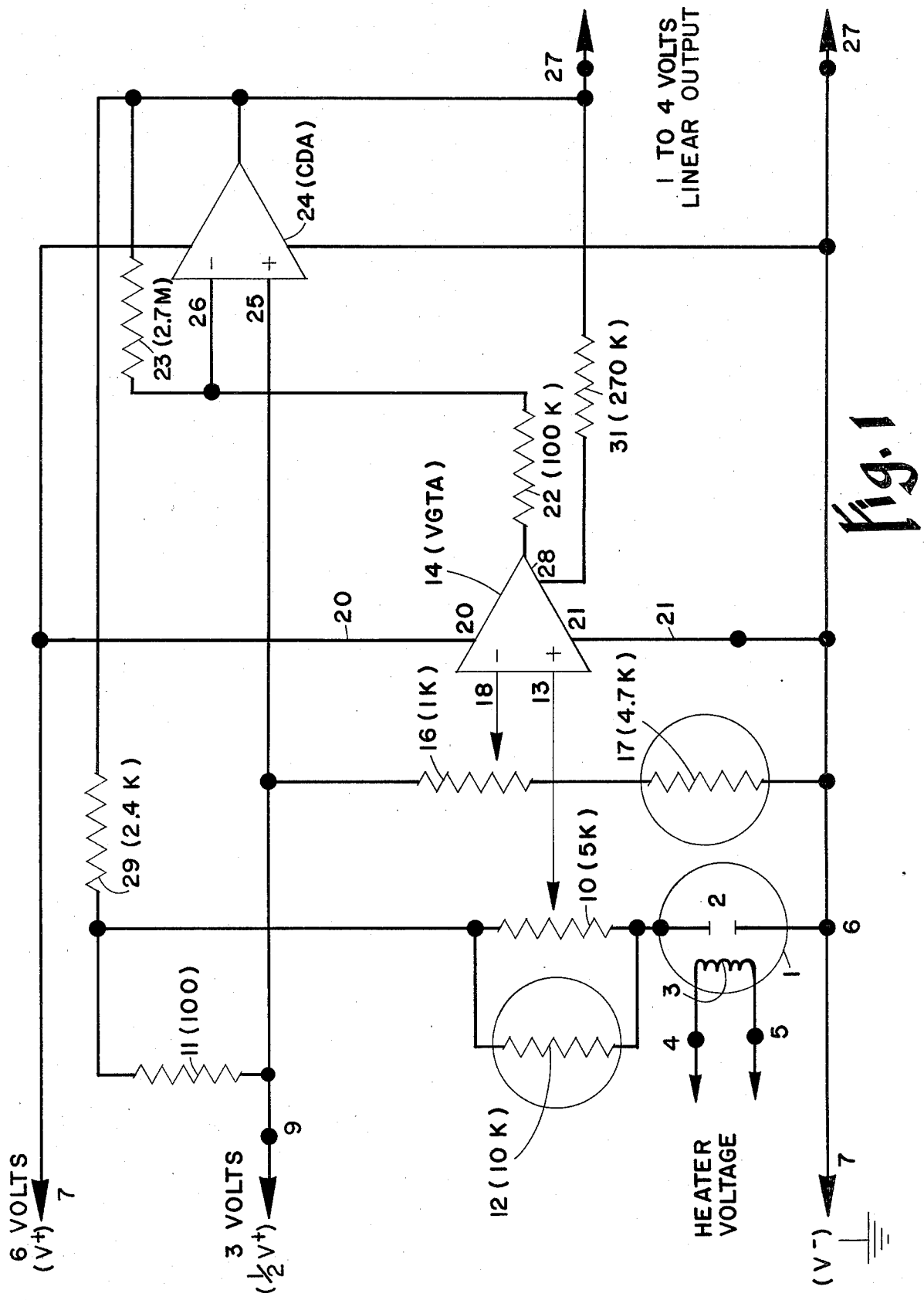
FIG. 1 is a schematic circuit diagram of the basic semiconductor gas sensor circuit incorporating the features of the present invention.

FIG. 1 shows the basic gas sensor circuit of this invention for the linearization of the semiconductor's gas concentration to voltage relationship. A semiconductor unit 1 suitable for operation as a gas sensor such as a Figaro Model No. 812 of the Taguchi type is placed in an atmosphere where a particular gas is to be detected. The semiconductor is sensitized for sensing a certain type of gas in a certain type of atmosphere such as, for example, the carbon monoxide concentrations encountered in parking garages. Those skilled in the art will, of course, realize that the principles disclosed in this circuit can be used to detect many other gas constituents in other industrial or safety situations. However, returning to the example of FIG. 1 we note that the electrical resistance of a semiconductor unit such as the Figaro Model No. 812 depicted in FIG. 1 does vary in relation to various carbon monoxide concentrations. This relationship is not usually linear, however, but rather varies according to a generally logarithmic curve which is not easily defined mathematically such as, for example, the one depicted as curve 1 in FIG. 2. The sensor unit 1 has a sensor element 2 and a heater element 3 which is connected by terminals 4 and 5 to a heater voltage source not shown. The operating temperature of the sensor unit 1 will to some extent depend on the composition of the gas mixture in the atmosphere being analyzed but generally will be between about 80° and 120° C. The semiconductor sensor element 2 is connected via its negative terminal 6 to the common of a first direct current source 7-7'. The positive terminal 8 of the sensor element 2 is connected to a second positive direct current source ($\frac{1}{2}$V+)9 via a first potentiometer 10 and a resistor 11 connected in series between said sensor element and said second positive direct current source. The voltage potential at 9 is about one half of the voltage potential of the first positive direct current source (V+)7'. In the circuit shown in FIG. 1, the voltage at 7' is preferably about 6 volts while the voltage at 9 is preferably about 3 volts. When no gas is present the resistance of the sensor element 2 is high and the voltage at the wipe point of said first potentiometer 10 will be near the ($\frac{1}{2}$V+) voltage at 9. When a gas constituent to be detected is present, the resistance of sensor element 2 decreases and the voltage at the wiper point of potentiometer 10 will drop in a non-linear fashion to produce a first output signal which varies non-linearly in accordance with the concentration of the gas constituent being detected.

A thermister 12 connected across the first potentiometer 10 serves the purpose of temperature compensating the sensor element 2 since sensor element 2 has a positive temperature coefficient while the thermister 12 has a negative temperature coefficient. For the carbon monoxide detection circuit shown in FIG. 1, thermister 12 is preferably rated at about 10,000 ohms at 25° C. It should be noted that thermister 12 does not contribute to the linearization functions of this circuit, but only serves the purpose of temperature compensating the sensor 1.

Potentiometer 10 forms a part of a voltage divider used to establish the amplification factor for the variable gain transconductance amplifier 14 such as for example a model LM 3080. Potentiometer 10 (preferably rated at about 5,000 ohms for the purposes of this circuit) helps set the overall range of this circuit. With the other values shown in this circuit, this first potentiometer 10 can set the gas level for maximum output (preferably at about 4 volts) from about 100 to 1000 parts per million of the carbon monoxide gas to be detected by this particular gas sensor circuit.

Via the first potentiometer 10, the positive terminal 8 of sensor element 2 is connected with the positive input terminal 13 (the non-inverting input of the variable gain transconductance of amplifier 14.) The desired potential for the positive input terminal 13 is obtained by setting the slider of the first potentiometer 10.

A second potentiometer 16 and a resistor 17 also form a voltage divider which contributes toward the determination of the amplification factor of the VGTA 14. That is, resistor 17 acts as the voltage dropping resistor to set the voltage range of potentiometer 16 to a convenient level. Those skilled in the art will also appreciate that resistor 17 could be deleted from the circuit without affecting the circuit's linear output characteristics.

Figure 2:
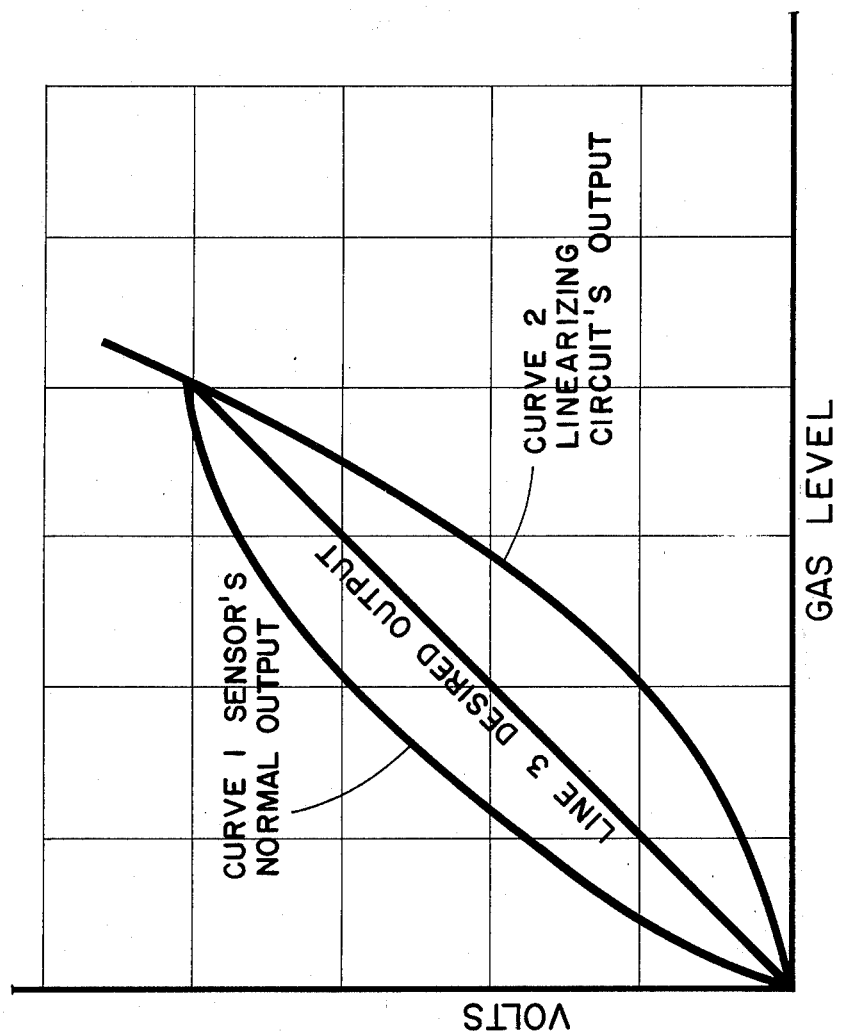
FIG. 2 is the graph of the gas concentration to voltage output for:
 (1) the gas sensor's normal output (curve 1),
 (2) the linearizing circuit's output (curve 2), and
 (3) the desired linear output (line 3) which results from the combination of curve 1 with curve 2.

The variable gain transconductance amplifier 14 is supplied with its necessary operating voltage (i.e., V+) via terminals 20 and 21, and will therefore differentially amplify the voltage differential at its two input terminals 13 and 18. Such variable gain transconductance amplifiers have been developed only rather recently and are chiefly characterized by the fact that they can be adjusted *internally* to a certain range of gain while the conventional differential amplifier (CDA) of the prior art must have their gains adjusted by external components. The degree of amplifications on the VGTA of this invention is determined by the bias current delivered to terminal 28 of the VGTA 14. Thus the variable gain transconductance amplifier with its ease of gain control becomes the main feature of this invention since it allows the gain to be smoothly and continuously varied over a desired operating range to achieve the linearization of the output of the semiconductor as shown in line 3 of FIG. 2. For example, when the atmosphere around the sensor element 2 contains no gas constituent of the type to be detected (i.e., carbon monoxide) the voltage at the zero point of the second potentiometer 16 will be slightly negative with respect to the voltage from potentiometer 10. In this state, the transconductance of the semiconductor unit 1 will be low (i.e., about 30 u mhos) and the output of the variable gain transconductance amplifier 14 will be slightly positive with respect to ($\frac{1}{2}$V+)9. When significant gas levels such as those indicated in FIG. 2 are present, then the voltage at potentiometer 10 will become more negative than the voltage at the wipe point of potentiometer 16 and the VGTA's transconductance will become higher (i.e., 100 u mhos or more) and hence the output of variable gain transconductance amplifier 14 will become significantly more negative. The gain of the variable gain transconductance amplifier 14 will then be a function of the product of the transconductance (u mhos) and the load resistance (ohms).

Figure 3:
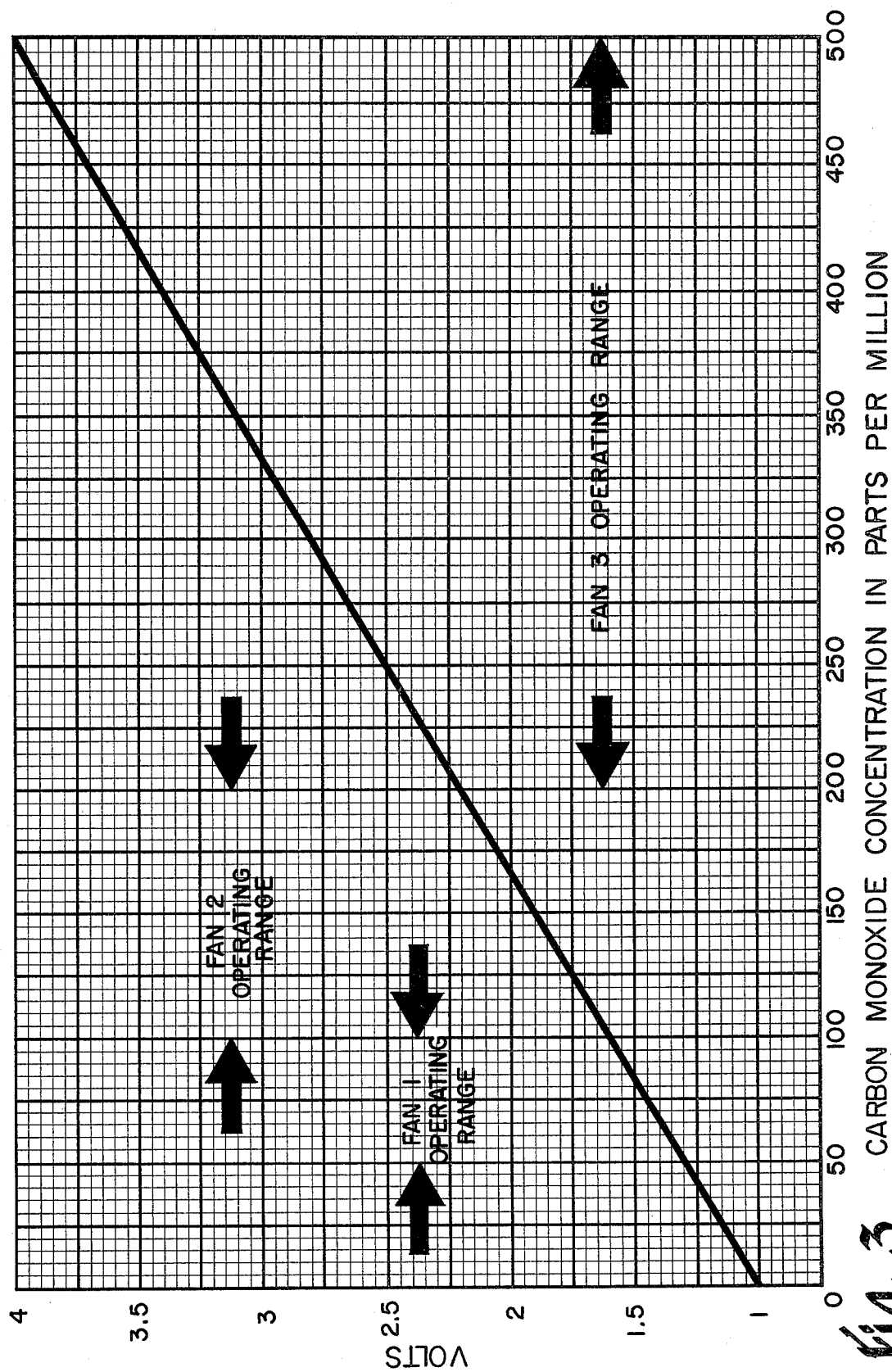
FIG. 3 is a graph of the output of this circuit adapted to linearize the voltage from 1 to 4 volts over a carbon monoxide concentration range of from about zero to about 500 parts per million of carbon monoxide.

The VGTA 14 thus produces a second output signal which goes through resistor 22 and feedback resistor 23 which are connected across the conventional differential amplifier 24 in order to set the gain of the CDA 24 to a fixed value (i.e., 2.7 M) as shown in FIG. 1. This fixed value gain, in conjunction with the size of resistor 31 and an attenuator formed by resistor 11 and resistor 29, sets the overall circuit gain. In the circuit shown in FIG. 1, resistor 22 should be about 100,000 ohms or more so as not to overload the output of the variable gain transconductance amplifier 14 which typically has a high impedance. The circuit values for this particular circuit are based on the use of $\frac{1}{2}$ of LM358 as the CDA, but other amplifiers can of course be used. It should also be noted that the second output signal is fed into the inverting terminal 26 of the CDA 24 so that a third output signal emanating from the CDA 24 will henceforth be seen as a positive voltage increase for an increase in gas concentration as depicted in FIG. 2 and FIG. 3.

As previously noted, resistors 29 and 11 serve as an attenuator on any negative feedback voltage from the third output signal of the conventional differential amplifier 24 back to the input at potentiometer 10. The circuit could perform without this negative feedback feature, but it would not have good long term stability, particularly at lower gas concentrations. The negative feedback stabilizes any potential drift because any attempted drifts are amplified by the differential amplifiers and fed back with the opposite phase to cancel the drift. The negative feedback also tends to help linearize the circuit's compensating function. Thus curve 2 of FIG. 2 would be more exaggerated in its curvature if the feedback were disconnected from the circuit. The ratio of resistor 29 to resistor 11 sets the straightness of the output (i.e., line 3 of FIG. 2). If resistor 11 gets larger, line 3 will tend to rise in the center and if resistor 11 were made smaller, line 3 would tend to drop somewhat in the center.

Resistor 31 in conjunction with the output voltage of conventional amplifier 24 determines the bias current to terminal 28 of the variable gain transductance amplifier 14 and hence its transconductance. The bias terminal 28 has an internal diode to common 7. As a result, this limits how low the output of the variable gain transconductance amplifier 14 can operate. Preferably this diode voltage is about 0.55 volts. In order to determine the bias current at any output condition of the CDA 24 the following formula is used:

$$I_{bias} = \frac{V_{out} - V_{diode}}{\text{Resistance of Resistor 31}}$$

For example, at Vout of 1 volt, Ibias = 1.66 u amps. At Vout of 4 volts, Ibias = 12.77 u amps. Thus over the range of 1 to 4 volts output, the bias to VGTA 14 will have varied over a range from about 1 to about 8. The transconductance of the VGTA 14 varies proportionally with this bias current. Naturally the resistance of resistor 31 could be made smaller so that the VGTA 14 would operate at a higher current if corresponding changes are made to resistors 22 and 23. The resistance of resistor 31 should not however be made much larger since the VGTA 14 will show some distortion if operated with a bias current below about one u amp.

Conventional differential operation amplifier 24 then compares the output of the variable gain transconductance amplifier 14 to the ($\frac{1}{2}$V+)9 reference voltage, and amplifies that difference by its set gain, i.e., the ratio of feedback resistor 23 to feedback resistor 31, in order to subsequently drive the outputs of both of these feedback resistors as well as the now linear third output signal going to output terminals 27 and 27' which may be connected to subsequent external operation performing components such as for example, fans, valves, alarms, computers, etc. With the circuit values shown in FIG. 1 the output of the conventional differential amplifier 24 would have an operating range of from about 1.0 volts to about 4.0 volts over a carbon monoxide range of from about zero to about 500 parts per million as depicted in FIG. 3.

The following is a listing of components (in addition to like identified components in FIG. 1 as identified hereinabove) that have been utilized in a working embodiment of one of the preferred forms of this invention, it being understood that such a listing is for illustrative purposes only and the invention is not meant to be limited thereto:

| Component reference number | | Value or designation |
|---|---|---|
| Resistors (ohms) | | |
| | R-11 | 100 |
| | R-17 | 4.7K |
| | R-22 | 100K |
| | R-23 | 2.7M |
| | R-29 | 2.4K |
| | R-31 | 270K |
| Semiconductor gas sensor | 1 | Figaro #812 |
| Potentiometer (ohms) | | |
| | R-10 | 5K |
| | R-16 | 1K |
| Thermister | R-12 | JA 41 J1 |

| Component reference number | | Value or designation |
|---|---|---|
| VGTA | 14 | LM 3080 |
| CDA | 24 | ½LM 358 |

FIG. 2 shows a series of graphs (not drawn to scale) for the gas concentration to voltage output relationship for:
(1) Curve 1, the gas sensor's concentration to voltage output, without sending said current through a VGTA, but after said output has been inverted by passing the sensor's normal output (which is characterized by a voltage drop for an increased gas concentration) through the inverting terminal of a CDA in the manner shown at terminal 26 of CDA 14 in FIG. 1.
(2) Curve 2, the linearization circuit's output after sending the gas sensor's normal output through the VGTA, CDA, resistors, etc. of FIG. 1.
(3) Line 3, the desired linear output for the circuit, which results from the combination of curves 1 and 2.

FIG. 3 shows the graph of the output (i.e., of the third output signal at terminals 27 and 27') of FIG. 3 specifically adapted to linearize the voltage from about 1 to about 4 volts over a carbon monoxide concentration range of from about zero to about 500 parts per million of carbon monoxide. This graph shows how the linear output can be used to operate one, two or three parking garage fans depending on gas concentration. That is, at gas concentrations of about 50 to 100 parts per million only one fan operates. At concentrations between 100 and 200 parts per million both fan 1 and fan 2 operate to remove the higher gas concentration. At concentrations above 200 parts per million all three fans will operate to remove the still higher carbon monoxide concentrations.

It will be appreciated that while this invention has been described with reference to the detection and elimination of carbon monoxide in air which might be inhaled by humans in a parking garage, the linearization principle of this invention is equally applicable to the detection of other gases which may be found in other types of environments such as gas pipelines, tanks, etc., and that said linear output is particularly useful in computer systems applications.

Thus having disclosed my invention what is claimed is:

1. In a gas detector circuit having a gas sensor of the semiconductor type, wherein the improvement in said circuit comprises:
(a) first direct current source having a common;
(b) second direct current source;
(c) semiconductor gas detector means disposed in gas communication with a gas constituent to be detected and having a sensor element means whose electrical resistance varies in accordance with the concentration of the gas constituent to be detected;
(d) first potentiometer resistor means connected in series with said sensor element means to form a voltage divider network therewith which is connected across the second direct current source and having an output wiper means upon which is established a first output signal which varies non-linearly in accordance with the concentration of the gas constituent to be detected;

(e) variable gain transconductance amplifier means (VGTA) having:
  (1) a pair of operating current terminals for supplying operating current from the first direct current source through the VGTA,
  (2) a non-inverting signal input terminal for receiving the first output signal from the wiper means of the first potentiometer resistor,
  (3) an inverting signal input terminal for receiving an input signal from a second potentiometer resistor,
  (4) a terminal for receiving a biasing current from the output voltage of a conventional differential amplifier (CDA) via a first feedback control resistor and thereby controlling the degree of amplification of said VGTA,
  (5) an output terminal for impressing a second output signal emanating from the VGTA and going to the CDA via a first gain control resistor;
(f) first gain control resistor connected in series with a second feedback control resistor between the VGTA and the second feedback control resistor;
(g) second potentiometer resistor which is series connected between the second direct current source and the common and having a wiper connected to the inverting signal input terminal of the VGTA;
(h) conventional differential amplifier (CDA) means having:
  (1) a pair of operating current terminals for supplying operating current from the first direct current source through the CDA,
  (2) a non-inverting signal input terminal connected to the second direct current source,
  (3) an inverting signal input terminal connected between the first gain control resistor and the second feedback control resistor,
  (4) an output terminal for impressing a third output signal emanating from the CDA which subsequently drives an external operation performing component.

2. The apparatus of claim 1 wherein the temperature coefficient of resistance of said semiconductor gas detector means is of negative sign and is temperature compensated by a thermister of positive sign which is bridged across said first potentiometer resistor means.

3. The apparatus of claim 1 wherein an attentuator comprising two series connected resistors which are connected in series between said second direct current source and the output terminal of said conventional differential amplifier means.

4. The apparatus of claim 1 wherein a resistor is connected in series between said second potentiometer means and said common of the first direct current source.

5. The apparatus of claim 1 wherein the external operation performing component is a computer system.

6. The apparatus of claim 1 wherein the external operation performing component is an alarm system.

7. The apparatus of claim 1 wherein the external operation performing component is a recording system.

8. The apparatus of claim 1 wherein the external operation performing component is an exhaust fan system.

9. The apparatus of claim 1 wherein the external operation performing component is a valve system.

10. The apparatus of claim 1 wherein the external operation performing component is a metering system.

* * * * *